(12) United States Patent
Kobold et al.

(10) Patent No.: US 7,807,401 B2
(45) Date of Patent: Oct. 5, 2010

(54) REAGENT FOR DIGESTION OF HEMOGLOBIN

(75) Inventors: Uwe Kobold, Weilheim (DE); Thomas Duelffer, Weilheim (DE); Rupert Herrmann, Weilheim (DE); Bernd Vogt, Tutzing (DE); Herbert von der Eltz, Weilhelm (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 29 days.

(21) Appl. No.: 12/330,725

(22) Filed: Dec. 9, 2008

(65) Prior Publication Data

US 2009/0246814 A1    Oct. 1, 2009

Related U.S. Application Data

(63) Continuation of application No. PCT/EP2007/006413, filed on Jul. 19, 2007.

(30) Foreign Application Priority Data

Jul. 21, 2006    (EP)   ................... 06015220

(51) Int. Cl.
*C12Q 1/37*    (2006.01)
(52) U.S. Cl. ...................................... 435/23
(58) Field of Classification Search .......... 435/23; 436/67
See application file for complete search history.

(56) References Cited

U.S. PATENT DOCUMENTS

| 5,631,140 | A | * | 5/1997 | Kobold et al. | .............. 435/23 |
| 5,882,935 | A | * | 3/1999 | Hirai et al. | .............. 436/67 |
| 6,027,907 | A | * | 2/2000 | Shinoki et al. | .............. 435/7.9 |
| 2004/0096932 | A1 | | 5/2004 | Kragl et al. | |
| 2005/0020814 | A1 | | 1/2005 | Rudolph et al. | |

FOREIGN PATENT DOCUMENTS

EP    0729031 A1    8/1996

OTHER PUBLICATIONS

Anson, L. et al., "The Estimation of Pepsin, Trypsin, Papain, and Cathepsin with Hemoglobin," J. Gen. Physiol 22 (1983) 79-89.
Benjamin, R. et al., "Glycated Protein Update: Implications of Recent Studies, Including the Diabetes Control and Complications Trial," Clin Chem 40:5 (1994) 683-687.
Goldstein, D. et al., "Glycated Hemoglobin: Methodologies and Clinical Applications," Clin. Chem. 32:10(B) (1986) B64-B70.
Goldstein, D. et al., "Is Glycohemoglobin Testing Useful in Diabetes Mellitus? Lessons from Diabetes Control and Complications Trial," Clin. Chem. 40:8 (1994) 1637-1640.
Jeppsson, J. et al., "Approved IFCC Reference Method for the Measurement of HbH1c in Human Blood," Clin Chem Lab Med 40:1 (2002) 78-89.
Nathan, et al., "The Effect of intensive Treatment of Diabetes on the Development and Progression of Long-Term Complications in Insulin-Dependent Diabetes Mellitus," The New England Journal of Medicine 329:14 (Sep. 30, 1993) 977-986.
Santiago, J. et al., "Lessons from the Diabetes Control and Complications Trial," Diabetes 42 (Nov. 1993) 1549-1554.
Tiran, A. et al., "Automated Determination of Glycated Hemoglobin: COmparative Evaluation of Five Assay Systems" Journal of Clinical Laboratory Analysis 8 (1994) 128-134.

\* cited by examiner

*Primary Examiner*—Ralph Gitomer
(74) *Attorney, Agent, or Firm*—Marilyn L. Amick; Roche Diagnostics Operations, Inc.

(57) ABSTRACT

The present invention relates to a reagent for digestion of hemoglobin comprising a buffer, pepsin and a 1,3-dialkyl-imidazolium salt. It also discloses to the use of this reagent in a method for digesting hemoglobin, in a method for detecting HbA1c, and to a sampling tube for collection of a whole blood sample comprising said reagent for digesting hemoglobin.

7 Claims, No Drawings

1

REAGENT FOR DIGESTION OF HEMOGLOBIN

RELATED APPLICATIONS

This application is a continuation of PCT/EP2007/006413 filed Jul. 19, 2007 and claims priority to European application EP 06015220.4 filed Jul. 21, 2006.

FIELD OF THE INVENTION

The present invention relates to a reagent for digestion of hemoglobin comprising a buffer, pepsin and a 1,3-dialkyl-imidazolium salt. It also discloses to the use of this reagent in a method for digesting hemoglobin, in a method for detecting HbA1c, and to a sampling tube for collection of a whole blood sample comprising said reagent for digesting hemoglobin.

BACKGROUND OF THE INVENTION

Impaired control of circulating blood glucose levels is the hallmark of diabetes. Blood glucose in a non-enzymatic statistical process may attach to the lysine residues of polypeptides thereby leading to glycated polypeptides. Glycation is frequently observed for proteins have a long half life. The protein most frequently used to assess long-term control of circulating blood glucose levels is hemoglobin.

There are numerous methods for determining glycated hemoglobin. These can be basically divided into three groups depending on the way in which glycated and non-glycated protein components are separated and quantified (Goldstein, D. E. et al., Clin. Chem. 32 Suppl. 10 (1986) B64-B70).

The first group consists of physicochemical methods based on the utilization of charge differences. These include the HPLC determination with cation exchanger columns such as Diamat, MonoS and PolyCat A (Bisse method) which are the most frequently used methods in clinical chemistry. In the case of glycated hemoglobin the quantitative evaluation is usually carried out by a relative measurement of the HbA1c signal in relation to the total amount of Hb (% HbA1c).

Methods in the second group are those which utilize the different chemical reactivity of glycated and non-glycated protein. These include the thiobarbituric acid method in which for example the glucose bound to hemoglobin is converted into a yellow dye and measured photometrically and also affinity chromatography methods in which complex formation between the vicinal diol groups of the sugar residue and a boric acid group that is bound covalently to a support is used to separate glycated and non-glycated hemoglobin. The separated substance classes are quantified photometrically and the relative amount of glycated hemoglobin is calculated or, in the case of the thiobarbituric acid method quantified, as an absolute determination by calibration with suitable standard materials.

Thirdly, immunological methods may be mentioned. Specific antibodies are used in immunological methods. These recognize for example the structural unit at the N-terminal end of the β chain of the glycated hemoglobin molecule which is typical for HbA1c (e.g., TINA-QUANT HbA1c, Roche Diagnostics GmbH, Germany). In the immunological methods the absolute content of both HbA1c and HbA0, respectively, is determined. This necessitates the use of calibrators which have been assigned a target concentration by an independent method. The relative content of for example HbA1c cannot be obtained by a direct measurement.

HbA1c is the major glycohemoglobin species in human blood. It has been used for almost 20 years for long-term assessment of glycemic control in diabetic patients. The comprehensive Diabetes Control and Complications Trial (DCCT) has provided ample evidence that microvascular complications such as retinopathy, nephropathy and neuropathy are directly related to the degree of hyperglycemia in patients with insulin-dependent diabetes (IDDM), and has proved that the measurement of $HbA_{1c}$ in blood is an excellent tool for long-term monitoring of the glycemic state of diabetic patients (The Diabetes Control and Complications Trial Research Group: The effect of intensive treatment of diabetes on the development and progression of long-term complications in insulin-dependent diabetes mellitus, Nathan et al., N. Engl. J. Med 329 (1993) 977-986: Santiago, J. V., Diabetes 42 (1993) 1549-1554; Benjamin, J. and Sacks, D. B., Clin. Chem. 40 (1994) 683-687; and Goldstein, D. et al., Clin. Chem. 40 (1994) 1637-1640). The DCCT study has also clearly demonstrated the need for reliable and reproducible measurements of HbA1c and HbA0—the normal nonglycated hemoglobin, respectively.

The known methods are, however, associated with a number of disadvantages. Thus some of the physicochemical methods have a very poor selectivity since the measured signals of glycated protein are overlapped by the non-glycated variants The shapes of the chromatographic peaks are often asymmetrical and difficult to integrate. The cation exchanger columns that are used are susceptible to small changes in the working conditions and to contamination. Due to the poor selectivity there is a high risk of measuring values that are too high (false positive values).

In the case of chemical methods it is difficult to standardize the procedure and interferences by other components containing sugar can only be avoided with a large amount of effort. It is not possible to differentiate between for example HbA1c and other glycated hemoglobin variants.

The immunological methods are characterized by a very high selectivity towards glycated protein variants. However, the quality of the results depends on the quality of the standard used for calibration. Suitable primary standards in an optimal quality are not at present available, in particular for HbA1c. Information on matrix dependencies cannot be obtained due to a lack of a suitable reference method. In this case false positive values are also frequently obtained (see for example Tiran, A. et al., J. Clin. Lab. Anal. 8 (1994) 128-134).

Kobold U., et al. (U.S. Pat. No. 5,631,140) describe a method for the detection of glycated proteins like hemoglobin that is based on the proteolytic digestion of proteins comprised in that sample. Detection of peptidic fragments is thereafter performed by high performance liquid chromatography (HPLC) and mass spectroscopy (MS). Recently, Jeppsson, J.-O. et al., Clin. Chem. Lab. Med. 40 (2002) 78-89 reported on a reference method for measurement of HbA1c that has been approved by the International Federation of Clinical Chemistry and Laboratory Medicine (IFCC). This method is based on the digestion of hemoglobin. Both the glycated and the non-glycated forms are enzymatically digested and the N-terminal peptide fragments of both forms of hemoglobin are quantified by HPLC-MS. In the enzymatic cleavage of hemoglobin endoproteinase Glu-C sequencing grade from Boehringer Mannheim, Mannheim, Germany (Id. no. 1047817) was used. To achieve complete digestion of hemoglobin an overnight digestion for e.g., 18 hours or a digestion with trypsin for 2 hours, respectively, is proposed.

Trypsin cleaves peptide bonds with lysine and arginine at the C-terminal side of the cleavage site, i.e., it cleaves between amino acids eight and nine of hemoglobin. Jeppsson et al., supra, were able to show that the lysine residues at position eight in the b-chain may also be glycated in samples with elevated HbA1c levels but not in those with normal levels. Thus using trypsin to release N-terminal octapeptides for quantification purpose would include the risk of getting doubly glycated octapeptides or singly glycated octapeptides glycated at the Lys-1 or at the Lys-8 position, respectively. Therefore these researchers concluded that trypsin cleavage was not usable. Endoproteinase Glu-C cleaves the N-terminal part of the b-chain between the two glutamic acid residues at positions six and seven. The resulting fragments contain only a single glycation site at the N-terminal valine and can thus be used to separate HbA1c. The actual cleaving site is easily exposed to the enzyme under mild denaturing conditions at pH 4.0. Complete denaturation prior to digestion exposes additional substrates to the enzyme and yields a more complex peptide mixture. By using the modern multidimensional analytical techniques of on-line HPLC and electrospray-mass spectrometry or the off-line system of HPLC and capillary electrophoresis the two β-N-terminal hexapeptides of HbA1c and HbA0 could be separated and quantified with the necessary analytical performance. Analyzing the mixture of peptide fragments resulting from the endoproteinase Glu-C digestion of whole blood samples, they obtained a high specificity and sensitivity in the measurement of HbA1c.

Some proteolytic enzymes lead to peptidic fragments that are likely to be generated at different rates. This in turn results either in a high variation of the concentration measured or in a rather long incubation time. A reagent used in the digestion of hemoglobin in order to assess the fraction of glycated hemoglobin should allow for both a rapid formation as well as for a stable formation of the desired peptidic fragments.

As will be appreciated, long digestion times go to the expense of sample throughput and are costly. For clinical routine a reagent ensuring the rapid digestion of hemoglobin and at the same time allowing for a precise quantization of e.g., HbA1c and HbA0 would be highly desirable. However, it appears that the methods for detection of hemoglobin that are based on the digestion of hemoglobin even nowadays require either quite long incubation times and/or do not lead to stable peptidic fragments.

It has now been found and established that a proteolytic reagent as disclosed below and as described in the appending claims can be provided that is very useful in the digestion of proteins and thereby e.g., leads to a rapid digestion of glycated and non-glycated hemoglobin.

SUMMARY OF THE INVENTION

The present invention relates to a reagent for digestion of hemoglobin comprising a buffer, pepsin and a 1,3-dialkyl-imidazolium salt consisting of a 1,3-dialkyl-imidazolium cation and a counter-ion.

Also disclosed is a method for digestion of hemoglobin the method comprising the steps of mixing a sample containing hemoglobin with a reagent according to this invention, digesting the hemoglobin for 1 to 60 min and thereby obtaining a fragment of hemoglobin consisting of the 14 N-terminal amino acids of hemoglobin.

Further disclosed is a method for measuring HbA1c the method comprising the steps of mixing a sample containing hemoglobin with a reagent for digestion of hemoglobin according to the present invention, digesting the hemoglobin for 1 to 60 min, thereby obtaining a fragment of HbA1c comprising the 14 N-terminal amino acids of HbA1c, measuring said N-terminal fragment of HbA1c, and correlating the value obtained to the concentration of HbA1c.

In a further embodiment the use of a 1,3-dialkyl-imidazolium salt consisting of the 1,3-dialkyl-imidazolium cation and a counter-ion in the digestion of hemoglobin by pepsin is described.

The invention also relates to a sampling tube comprising a reagent composition for digestion of hemoglobin as disclosed in the present invention.

DETAILED DESCRIPTION OF THE INVENTION

In a first embodiment the present invention relates to a reagent for digestion of hemoglobin, the reagent comprising a) a buffer, b) pepsin and c) a 1,3-dialkyl-imidazolium salt consisting of a 1,3-dialkyl-imidazolium cation and a counter-ion.

The reagent or reagent mixture disclosed can be used to efficiently digest hemoglobin. The enzymatic digestion is brought about by pepsin. Pepsin is one of three principal protein-degrading, or proteolytic, enzymes in the digestive system, the other two being chymotrypsin and trypsin. The three enzymes were among the first to be isolated in crystalline form. During the process of digestion, these enzymes, each of which is particularly effective in severing links between particular types of amino acids, collaborate to break down dietary proteins to their components, i.e., peptides and amino acids, which can be readily absorbed by the intestinal lining.

Pepsin is synthesized in an inactive form by the stomach lining; hydrochloric acid, also produced by the gastric mucosa, is necessary to convert the inactive proenzyme or zymogen into the active enzyme and to maintain the optimum acidity (pH 1-3) for pepsin function. There are several pepsins designated A, B, C, and D. Pepsin A, the major component, has a molecular weight of 35,000 Daltons and an optimum pH of approximately 1.0 for substrates such as casein or hemoglobin if the substrate is native protein. Pepsin cleaves proteins preferentially at carboxylic groups of aromatic amino acids such as phenylalanine and tyrosine. It will not cleave at bonds containing valine, alanine or glycine. Its action breaks long polypeptide chains into shorter length peptides.

The reagent according to the present invention is buffered to ensure rapid and efficient action of pepsin. Since pepsin is most active at a strongly acidic pH the buffer will preferably be adjusted to a pH between pH 1 and pH 4. Also preferred the pH will be between pH 1.5 and pH 3.

The skilled artisan will have no problem in choosing an appropriate pH as well as an appropriate buffer system. Acidic buffer systems can for example be based on glycine, or on citrate. Preferably HCl is used to adjust the pH as desired The concentration of the buffer is adjusted to ensure an appropriate pH in the digestion of hemoglobin. Preferably the buffer has a concentration of between 10 mM and 1 M. Also preferred the buffer will have a concentration of 50 to 200 mM.

Pepsin (E.C.3.4.23.1) is assayed based on the method of Anson, M. L., J. Gen. Physiol. 22 (1938) 79-89 using hemoglobin as the substrate. Unit Definition: One unit causes an increase in absorbance at 280 nm of 0.001/min at 37° C., pH 2.0. Preferably in the reagent according to the present invention pepsin is present in a concentration of between 30 and 6000 U/ml.

As discussed above, pepsin if used in the digestion of hemoglobin under normal digestion conditions, aside to the generation of other peptidic fragments, leads to the formation of two N-terminal fragments with 7 and 14 amino acids, respectively. Since these two peptides are formed at different rates no reliable determination of HbA1c, e.g., by measuring the 14 amino acid peptide is possible. It has been found and is demonstrated in the examples section that pepsin in the presence of a 1,3-dialkyl-imidazolium salt leads to both a rapid as well as a stable formation of the N-terminal 14 amino acid peptide fragment of hemoglobin. The reagent according to the present invention therefore comprises a 1,3-dialkyl-imidazolium salt.

Formula I: 1,3-dialkyl-imidazolium salt

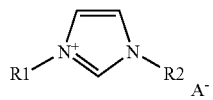

wherein R1 and R2 independently represent alkyl residues and, wherein A⁻ represents a counter ion.

Preferably the alkyl residues of the 1,3-dialkyl-imidazolium salt comprised in a reagent according to the present invention are selected from methyl, ethyl, propyl, isopropyl, butyl, or isobutyl. Also preferred two alkyl residues in said 1,3-dialkyl-imidazolium are independently selected from methyl, ethyl or propyl.

The reagent according to the present invention will comprise the 1,3-dialkyl-imidazolium salt in an appropriate concentration to achieve the advantageous effects on pepsin activity and protein digestion. Preferably it is comprised in a final concentration from 1 to 25%. Also preferred the concentration of the 1,3-dialkyl-imidazolium salt in aregaent according to the present invention will be in the range from 2 to 20% or from 4 to 15%.

As the skilled artisan will readily appreciate the counter ion contained in the 1,3-dialkyl-imidazolium salt will contain a negative charge and is not crucial. Preferably the counter-ion is selected from phosphate, alkylphosphate, sulfate and alkylsulfate.

The reagent mixture according to the present invention has proven advantageous in the digestion of hemoglobin and is expected to be advantageous in the digestion of any protein as for example comprised in human serum. The more rapid and more constant action of pepsin is expected to be seen in analogy with any other polypeptide of interest. This will facilitate the analysis of the overall serum protein composition or of other individual proteins comprised therein.

In a further embodiment the present invention relates to a method for digestion of hemoglobin the method comprising the steps of a) mixing a sample containing hemoglobin with a reagent according to the present invention, and b) digesting the hemoglobin for 1 to 60 min, thereby obtaining a fragment of hemoglobin consisting of the 14 N-terminal amino acids of hemoglobin.

The method for digestion of hemoglobin is preferably used in the measurement of hemoglobin and/or glycated hemoglobin, respectively.

In a preferred embodiment the present invention relates to a method for measuring HbA1c the method comprising the steps of a) mixing a sample containing hemoglobin with a reagent according to the present invention, b) digesting the hemoglobin for 1 to 60 min, thereby obtaining a fragment of hemoglobin consisting of the 14 N-terminal amino acids of HbA1c, and c) measuring said N-terminal fragment of HbA1c.

The present invention also relates to a method for measuring the relative concentration of HbA1c in total hemoglobin the method comprising the steps of mixing sample containing hemoglobin with a reagent for digestion of hemoglobin the reagent comprising (a) a buffer, (b) pepsin and (c) a 1,3-dialkyl-imidazolium salt consisting of a 1,3-dialkyl-imidazolium cation and a counter-ion, digesting the hemoglobin for 1 to 60 min, thereby obtaining a fragment of hemoglobin consisting of the 14 N-terminal amino acids of hemoglobin that is either glycated or non-glycated, respectively, measuring both said N-terminal glycated and said N-terminal non-glycated fragment of hemoglobin, respectively, and correlating the values obtained in (c) to the relative concentration of HbA1c in total hemoglobin.

As shown in the examples with the reagent mixture according to the present invention it is possible to digest hemoglobin extremely fast, i.e., maximum digestion is already seen after about one minute. It has also been found the peptide fragment consisting of the 14 N-terminal amino acids of hemoglobin stays stable for at least one hour. This is true for both the non-glycated (HbA0) as well as the glycated HbA1c N-terminal peptidic fragment, respectively. These findings greatly facilitates samples handling and allows for a flexible timing of measurements of HbA0 and HbA1c, respectively. Due to these stable measurements the calculation of % HbA1c is not subject to extensive variation and thus rather precise and reliable.

The N-terminal 14 amino acid fragments of HbA0 and HbA1c, respectively, can be quantified by any appropriate means. In a preferred embodiment quantification is achieved by immunological procedures. In a further preferred embodiment measurement of these peptides is performed by HPLC and mass spectroscopy.

A further preferred embodiment relates to the use of a 1,3-dialkyl-imidazolium salt consisting of the 1,3-dialkyl-imidazolium cation and a counter-ion in the digestion of a protein by pepsin. Further preferred the present invention relates to the use of a 1,3-dialkyl-imidazolium salt consisting of the 1,3-dialkyl-imidazolium cation and a counter-ion in the digestion of hemoglobin by pepsin.

It may be desirable and advantageous to directly collect a whole blood sample into a sampling tube containing a reagent according to the present invention. In a preferred embodiment the invention therefore also relates to a sampling tube comprising a reagent composition according to the present invention.

The following examples are provided to aid the understanding of the present invention, the true scope of which is set forth in the appended claims. It is understood that modifications can be made in the procedures set forth without departing from the spirit of the invention.

EXAMPLE 1

General Procedure for Proteolysis of Hemoglobin (Hb)

An aliquot of 24 microliter hemoglobin solution containing 0.2 mg/mL of hemoglobin and 50 mM ammonium acetate (pH 4.3) is mixed with 216 µl of a solution containing pepsin (300 U/mL) in 20 mM citric acid pH 2.4 and optionally a 1,3-dialkyl-imidazolium salt (10% weight/volume). The reaction solution is kept at room temperature until measurement. Measurement is done with HPLC-MS (cf. example 2) after digestion times of 1 minute, 11, 21, 31,41, 51 and 61 minutes, respectively. The amount of N-terminal peptides [1-14] derived from the HbA0 and from the HbA1c beta chain as released upon pepsin digestion and the ratio of these peptides (HbA1c per HbA0) are reported.

EXAMPLE 2

Measurement of HbA0 and HbA1c N-terminal Peptides with HPLC-MS

10 µL of the digest as obtained in example 1 are injected into the HPLC.

The HPLC system consists of an HP 1090 liquid chromatograph (Agilent) with an DR 5 solvent delivery system, a thermostats equipped autosampler, an autoinjector and a diverte valve between HPLC and mass spectrometer. Detector is a linear ion trap mass spectrometer, Thermo Electron LTQ, with electrospray ionisation. For chromatographic separation a HPLC column having Symmetry, C18 particles as bed material, an inner column diameter of 2 mm, column length of 200 mm and a frit with 0.5 μm pore size is used. The eluent is a gradient from water with 0.1% formic acid (A) to acetonitrile with 0.1% formic acid (B), 1 minute 100% A, within 4 minutes to 15% B and thereafter within 2 minutes to 50% B. The flow rate is 0.2 mL/min. HbA0 and HbA1c peptides [1-14] elute at approximately 4.4 to 5.2 minutes, respectively. Detection is done by MS/MS transition, HbA0 m/z 748.5 to 683.2 and HbA1c m/z 829.1 to 802.0.

The results for digestion of hemoglobin as obtained by adding either 1-ethyl-3-methylimidazolium ethylsulfate, 1-butyl-3-methylimidazolium methylsulfate or without addition of a 1,3-dialkyl-imidazolium salt are given in Tables 1 to 3, respectively.

TABLE 1

Digestion results for 1-ethyl-3-methylimidazolium ethylsulfate

| | 1-ethyl-3-methylimidazolium ethylsulfate | | |
| --- | --- | --- | --- |
| T[min.] | 748.5 -> 683.2 area(ms2) A0 β[1-14] | 829.1 -> 802.0 area(ms2) A1c β[1-14] | ratio A1c/A0 β[1-14] |
| 1 | 561880 | 319759 | 0.5691 |
| 11 | 559011 | 304845 | 0.5453 |
| 21 | 538150 | 283047 | 0.5260 |
| 31 | 524271 | 278103 | 0.5305 |
| 41 | 502545 | 277339 | 0.5519 |
| 51 | 488469 | 269000 | 0.5507 |
| 61 | 482869 | 268930 | 0.5569 |
| avg | 522456 | 285860 | 0.547 |
| s | 32298 | 19240 | 0.01 |
| VK(%) | 6 | 7 | 3 |
| VK(%)n.11 min | 6 | 5 | 2 |
| VK(%)n.21 min | 5 | 2 | 3 |

TABLE 2

Digestion results for 1-butyl-3-methylimidazolium methylsulfate

| | 1-butyl-3-methylimidazolium methylsulfate | | |
| --- | --- | --- | --- |
| T[min.] | 748.5 -> 683.2 area(ms2) A0 β[1-14] | 829.1 -> 802.0 area(ms2) A1c β[1-14] | ratio A1c/A0 β[1-14] |
| 1 | 480903 | 271838 | 0.5653 |
| 11 | 543371 | 281675 | 0.5184 |
| 21 | 510676 | 280444 | 0.5492 |
| 31 | 483673 | 289468 | 0.5985 |
| 41 | 496431 | 276577 | 0.5571 |
| 51 | 472372 | 269102 | 0.5697 |
| 61 | 478487 | 256608 | 0.5363 |
| avg | 495130 | 275102 | 0.556 |
| s | 24830 | 10559 | 0.03 |
| VK(%) | 5 | 4 | 5 |
| VK(%)n.11 min | 5 | 4 | 5 |
| VK(%)n.21 min | 3 | 5 | 4 |

TABLE 3

Digestion results without imidazolium salt

| | Without imidazolium salt | | |
| --- | --- | --- | --- |
| T[min.] | 748.5 -> 683.2 area(ms2) A0 β[1-14] | 829.1 -> 802.0 area(ms2) A1c β[1-14] | ratio A1c/A0 β[1-14] |
| 1 | 515579 | 267266 | 0.5184 |
| 11 | 565225 | 343742 | 0.6082 |
| 21 | 588113 | 314792 | 0.5353 |
| 31 | 499632 | 349421 | 0.6994 |
| 41 | 511829 | 347366 | 0.6787 |
| 51 | 592245 | 349365 | 0.5899 |
| 61 | 589784 | 343078 | 0.5817 |
| avg | 551772 | 330719 | 0.602 |
| s | 41248 | 30487 | 0.07 |
| VK(%) | 7 | 9 | 11 |
| VK(%)n.11 min | 7 | 4 | 10 |
| VK(%)n.21 min | 8 | 4 | 11 |

What is claimed is:

1. A method for measuring HbA1c in a sample comprising the steps of
   mixing a sample containing hemoglobin with a reagent under conditions for digestion of the hemoglobin, the reagent comprising a buffer, pepsin, and a 1,3-dialkyl-imidazolium salt consisting of a 1,3-dialkyl-imidazolium cation and a counter-ion,
   digesting the hemoglobin for 1 to 60 minutes, thereby obtaining a fragment of hemoglobin comprising a 14 N-terminal amino acids of HbA1c, and
   measuring said fragment of HbA1c and correlating the measure of the fragment to the amount of HbA1c in the sample.

2. The method according to claim 1, wherein the buffer has a pH between 1 and 4.

3. The method according to claim 1, wherein the buffer has a concentration between 10 mM and 1 M.

4. The method according to claim 1, wherein the pepsin is present in the reagent in a concentration between 30 and 6000 U/ml.

5. The method according to claim 1, wherein the two alkyl residues of the 1,3-dialkyl-imidazolium salt are independently selected from the group consisting of methyl, ethyl and propyl.

6. The method according to claim 1 wherein the counter-ion is selected from the group consisting of phosphate, alkylphosphate, sulfate and alkylsulfate.

7. A method for digestion of hemoglobin comprising the steps of
   mixing a sample containing hemoglobin with a with a reagent under conditions for digestion of hemoglobin, the reagent comprising a buffer, pepsin, and a 1,3-dialkyl-imidazolium salt consisting of a 1,3-dialkyl-imidazolium cation and a counter-ion, and
   digesting the hemoglobin for 1 to 60 minutes, thereby obtaining a fragment of hemoglobin comprising a 14 N-terminal amino acids of hemoglobin.

* * * * *